United States Patent
Dart et al.

(10) Patent No.: US 9,122,776 B2
(45) Date of Patent: Sep. 1, 2015

(54) ENHANCED ELECTRONIC HEALTH RECORD GRAPHICAL USER INTERFACE SYSTEM

(71) Applicant: ADP, LLC, Roseland, NJ (US)

(72) Inventors: Stephen Dart, Eltopia, WA (US); Matthew Barron, West Jordan, UT (US); Jared Rich, Midvale, UT (US); Lisa Louvar, Lehi, UT (US); Jared Alviso, Herriman, UT (US)

(73) Assignee: ADP, LLC, Roseland, NJ (US)

( * ) Notice: Subject to any disclaimer, the term of this patent is extended or adjusted under 35 U.S.C. 154(b) by 318 days.

(21) Appl. No.: 13/834,933

(22) Filed: Mar. 15, 2013

(65) Prior Publication Data

US 2014/0282238 A1     Sep. 18, 2014

(51) Int. Cl.
  *G06F 3/0482* (2013.01)
  *G06F 19/00* (2011.01)
  *G06Q 50/22* (2012.01)
  *G06F 3/0481* (2013.01)
  *G06Q 50/24* (2012.01)

(52) U.S. Cl.
  CPC ............ *G06F 19/322* (2013.01); *G06F 3/0482* (2013.01); *G06F 3/04817* (2013.01); *G06F 19/32* (2013.01); *G06F 19/324* (2013.01); *G06F 19/327* (2013.01); *G06F 19/36* (2013.01); *G06Q 50/22* (2013.01); *G06Q 50/24* (2013.01)

(58) Field of Classification Search
  CPC ..... G06F 19/322; G06F 19/32; G06F 19/324; G06F 19/327; G06F 19/36; G06F 3/0482; G06F 3/04817; G06Q 50/24; G06Q 50/22
  See application file for complete search history.

(56) References Cited

U.S. PATENT DOCUMENTS

| | | | |
|---|---|---|---|
| 8,151,204 B2 * | 4/2012 | Lusen et al. | 715/769 |
| 2004/0163049 A1 * | 8/2004 | Mori et al. | 715/527 |
| 2006/0206807 A1 * | 9/2006 | Rosner et al. | 715/515 |
| 2007/0227537 A1 * | 10/2007 | Bemister et al. | 128/200.24 |
| 2008/0034117 A1 * | 2/2008 | Lemay et al. | 709/245 |
| 2008/0288300 A1 * | 11/2008 | Emling et al. | 705/4 |
| 2008/0294479 A1 * | 11/2008 | Emling et al. | 705/7 |
| 2008/0300922 A1 * | 12/2008 | Forgue et al. | 705/3 |
| 2014/0282238 A1 * | 9/2014 | Dart et al. | 715/810 |

* cited by examiner

*Primary Examiner* — Ting Lee
(74) *Attorney, Agent, or Firm* — Joseph V. Saphia; Frommer Lawrence & Haug LLP (57) ABSTRACT

An enhanced electronic health record system. A user device having a display accesses electronic health records and clinic note templates stored on digital storage segments. A template selection screen is presented on the display of the user device. The template selection screen has at least two view modes. One view mode is a grid view, in which icon representations of various clinic note templates are displayed, each icon representation having a number of secondary icons providing additional functionality and information to the user. Also available is a list view, which also contains a vertical listing of available clinic note templates, each list element also having secondary icons. Upon selection of a template, the user is presented with a formatted clinic note. Additional functionality is available to the user to aid in the efficient capture of information.

17 Claims, 14 Drawing Sheets

ENHANCED ELECTRONIC HEALTH RECORD GRAPHICAL USER INTERFACE SYSTEM

FIELD OF THE DISCLOSURE

The subject matter of the present disclosure generally relates to electronic health record systems, and more particularly relates to a graphical user interface with which to capture clinical notes.

BACKGROUND OF THE DISCLOSURE

Electronic health record (EHR) systems have been previously disclosed. Such systems can present certain difficulties for health care providers seeking to create and fill patient clinical notes. Users must often create and format new clinic notes from scratch, leading to inconsistent formatting and ultimately the omission of important information. Where templates for clinic notes do exist, they are often stored in manners that are difficult to navigate. Providers are often required to manually reenter certain patient information, such as age, sex, or patient number, repeatedly. Providers are also often forced to switch back and forth between screen views to collect and enter the necessary information to build a complete clinical note.

These difficulties are compounded for users operating on mobile electronic devices, the functionality of which can be constrained by screen size. The use of text-rich graphical user interfaces slows down the user-provider, encumbers the user's resources, and requires the user to visually scan the display for long lengths of time to find a desired data or function.

The subject matter of the present disclosure is directed to overcoming, or at least reducing the effects of, one or more of the problems set forth above.

BRIEF SUMMARY OF THE DISCLOSURE

Disclosed is a system for the management of EHRs and the creation and management of clinic notes. A user with an electronic device is presented a graphical user interface having a template selection screen on which the user can select a template from which to build a clinical note. The template selection screen can be viewed in either a grid or a list view. In the grid view, templates are represented as large icons, each such representation having a number of associated secondary icons. These secondary icons immediately provide additional information to the user, such as by indicating that a template is on the user's favorites list. They also provide additional functionality when selected, such as providing a brief summary of the associated template.

When a user selects a template to use from the template selection screen, a clinic note is created. The created note is pre-formatted according to the selected template to aid the user in collecting relevant information. For instance, a template regarding environmental allergens may have a list of possible allergens about which the provider may inquiry with the patient. Other functionality is provided to the user, such as the automatic completion of acronyms and the ability to drop "bookmarked" information about a patient directly into a clinical note. These enhancements can improve the speed with which a provider can capture data. Iconography is used to convey information quickly and succinctly. This can be advantageous to users operating on mobile electronic devices, which often have limited screen sizes and thus limited screen "real estate." The informed use of templates allows a user to quickly create desired notes, freeing time to interact with the patient.

The details of one or more embodiments of the invention are set forth in the accompanying drawings and descriptions below. The foregoing summary is not intended to summarize each potential embodiment or every aspect of the disclosure.

BRIEF DESCRIPTION OF THE DRAWINGS

The foregoing summary, preferred embodiments, and other aspects of subject matter of the present disclosure will be best understood with reference to a detailed description of specific embodiments, which follows, when read in conjunction with the accompanying drawings, in which.

Like reference numbers and designations in the various drawings indicated like elements.

DETAILED DESCRIPTION OF THE DISCLOSURE

Disclosed is an enhanced electronic health record (EHR) system. Clinic note templates and EHRs are stored on digital storage segments and accessed by a user device. The user device presents to the user a graphical user interface which allows the user to easily create and management clinic notes. Where identified below, virtual "buttons," drop-down menus, icons and similar items are understood to be elements presented on the display of an electronic device and "selectable" or capable of being manipulated by user input to an electronic device. User input is understood to encompass a wide variety of circumstances. For instance, user input could be text entry via a keyboard or selection of a virtual object via a computer mouse or similar selection instrumentality.

Figure 1:
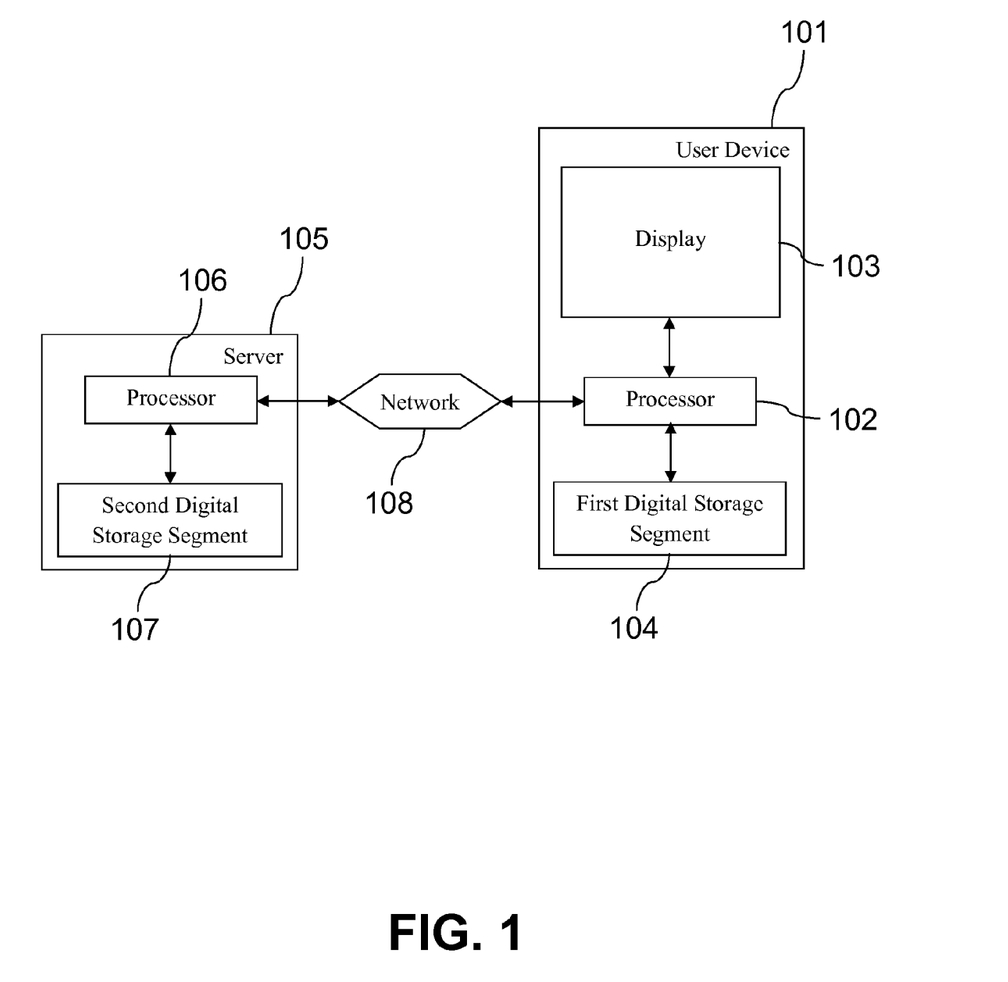
FIG. 1 is a diagram of an embodiment of the disclosed system in which an electronic user device is connected to a remote server and where both the server and the user device have a digital storage segment.

FIG. 1 is a diagram of an embodiment in which a user device is connected to a remote server. User device 101 has processor 102, display 103 and first digital storage segment 104. User electronic device 101 is capable of receiving user input from a user. Optionally, display 103 of user electronic device 101 is an electronic touch screen and user input is the interaction of a user with the touch screen. First digital storage segment has encoded on it a number of clinic note templates. Server 105 has processor 106 and second digital storage segment 107. For the purposes of this application, a digital storage segment is any digital storage area, and optionally two comingled portions of a single hard drive or other storage medium or two separate hard drives or other storage medium. Second digital storage segment 107 has encoded on it a number of health records, each record associated with a particular patient. The storage of clinic note templates on a digital storage segment local to a user device in combination with the storage of EHRs on a remote digital storage segment can be advantageous. Independently, personal health information is compromised if the user device is lost or stolen. Simultaneously, the local storage of clinic note templates can allow better performance of the graphical user interface.

Processor 102 of user device 101 communicates with processor 106 of server 105 through network 108. Particularly, processor 102 of user device 101 is effective to access the clinic note templates encoded on the first digital storage segment and EHRs encoded on the second digital storage segment. User device 101 is effective to present on display 103 a template selection screen containing representations of a portion of the clinic note templates. User device 101 can present on display 103 numerous aspects of the disclosed subject matter, which are discussed below.

Figure 2:
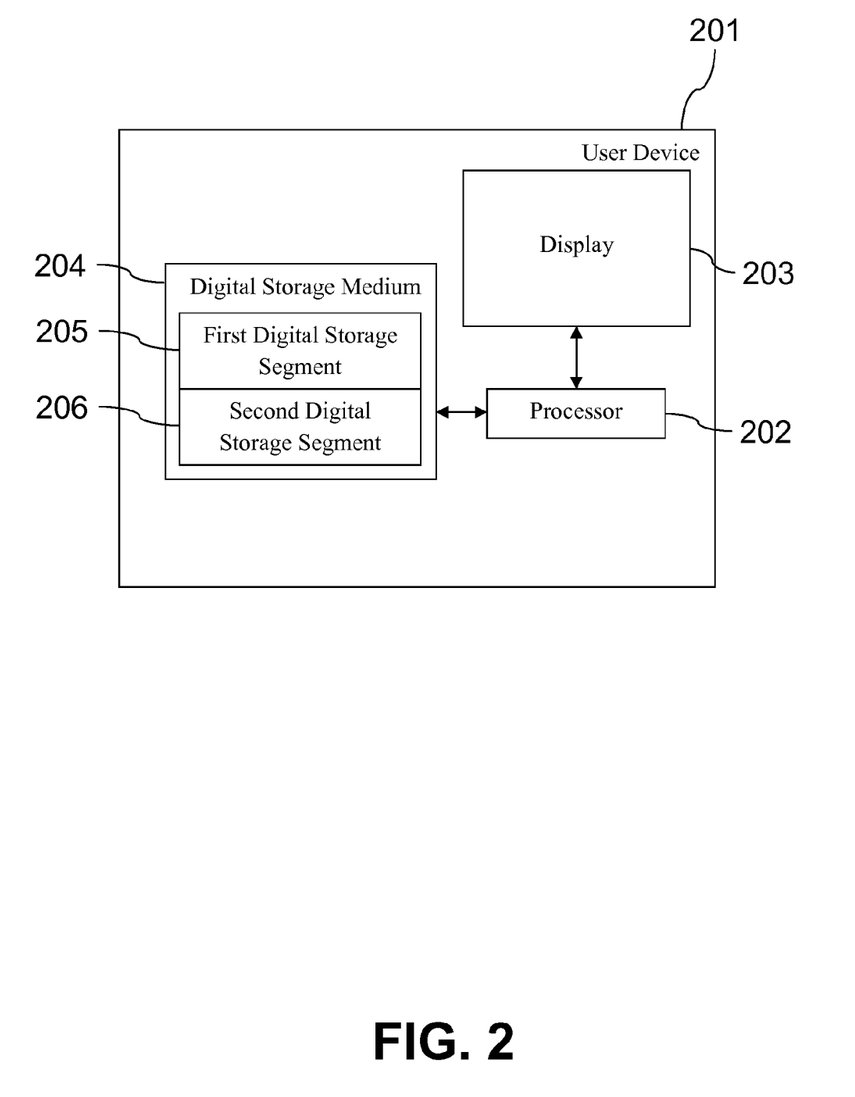
FIG. 2 is a diagram of an embodiment of the disclosed system in which an electronic device has a local digital storage medium.

FIG. 2 is a diagram of an alternate embodiment in which user device 201 has processor 202, display 203, and digital storage medium 204, which is comprised of a first digital storage segment 205 and second digital storage segment 206. Clinic note templates are encoded on storage segment 205 and EHRs are encoded on storage segment 206.

Figure 3:
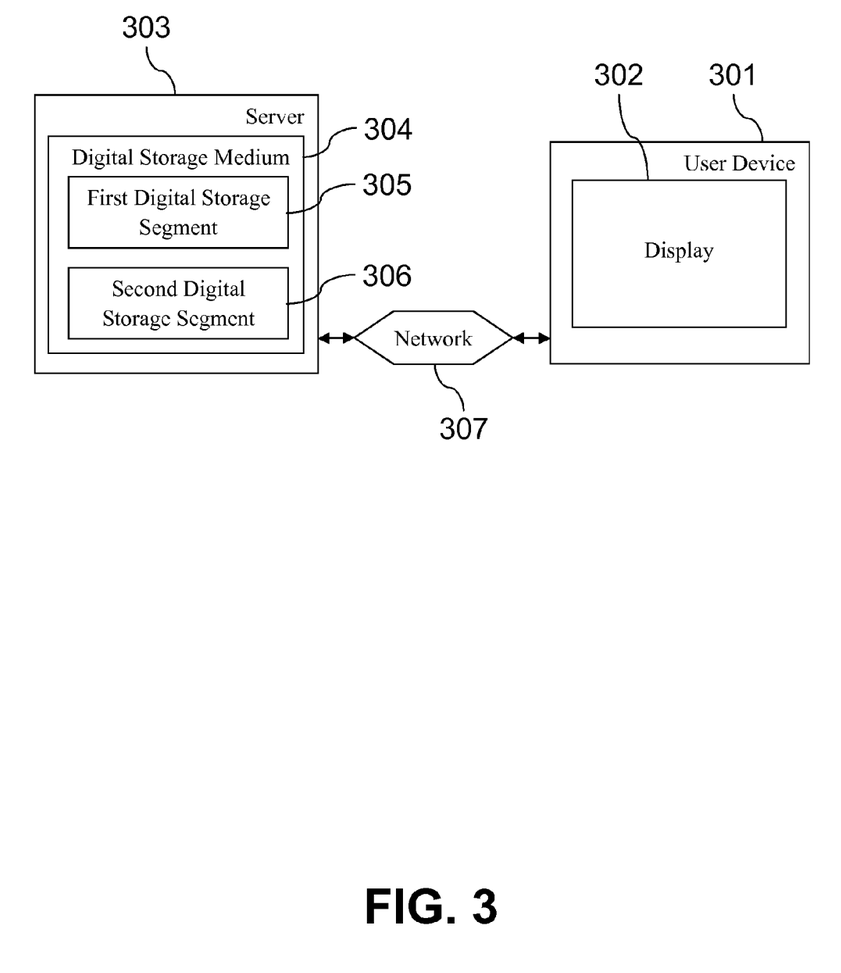
FIG. 3 is a diagram of an embodiment of the disclosed system in which all encoded storage is accomplished entirely on a remote storage medium.

FIG. 3 is a diagram of an alternate embodiment in which both clinic note templates and health records are stored remotely from a user device. User device 301 has display 302. Server 303 has digital storage medium 304, which is comprised of first digital storage segment 305 and second digital storage segment 306. User device 301 communicates with server 303 through network 307.

FIGS. 4-14 are illustrations of an exemplary embodiment of the disclosure, and it is understood that their content does not limit the scope of the disclosed subject matter or claims.

Figure 4:
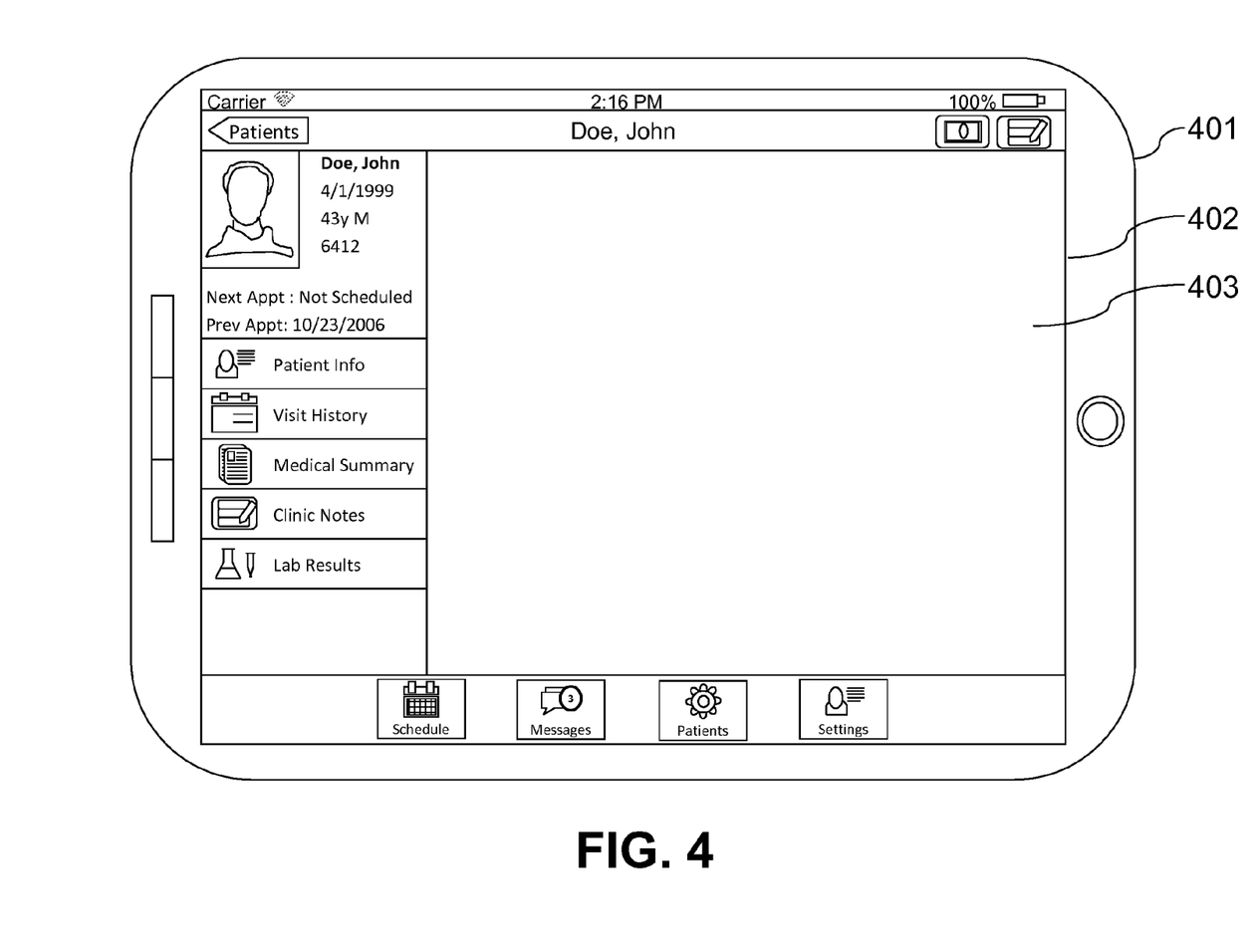
FIG. 4 is an illustration of an embodiment in which a basic graphical user interface is presented on the display of an electronic device.

FIG. 4 is an illustration of an embodiment in which user device 401 has display 402. Display 402 is capable of presenting to the user graphical user interface 403.

Figure 5:
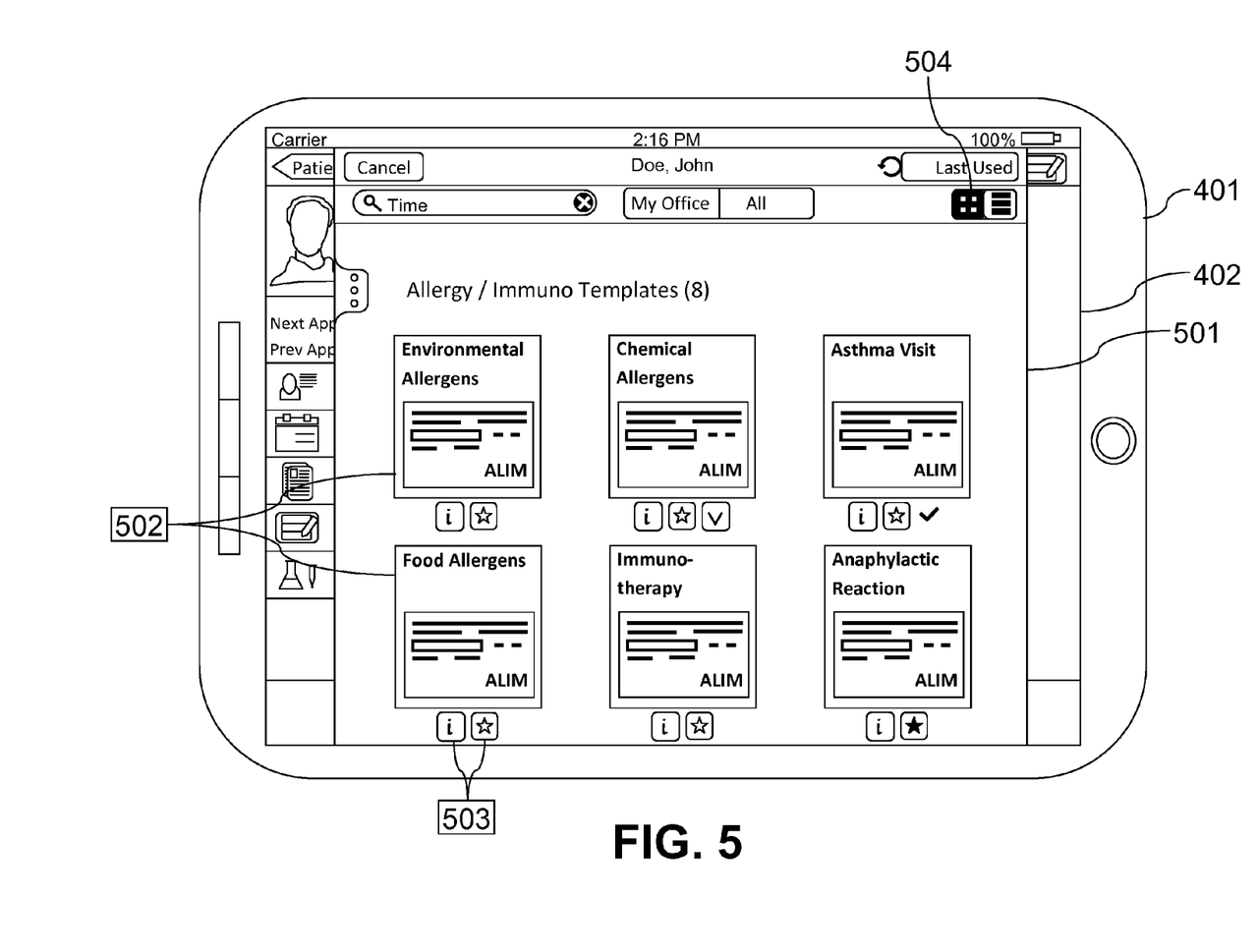
FIG. 5 is an illustration of an embodiment in which a user device presents a grid view of template representations.

FIG. 5 is an illustration of an embodiment in which display 402 presents template selection screen 501 in a grid view. Template selection screen 501 has clinic note template representations 502. In FIG. 5, clinic note template representations 502 are template icons. Each template icon has a number of associated secondary icons 503 presented on display 402 in proximity to the template icon. View selector icon 504 indicates that the view is a grid view and allows the user to switch between grid and list views. Template selection screen 501 and other aspects of the disclosure can optionally be accessed and presented through an Internet browser application.

Figure 6:
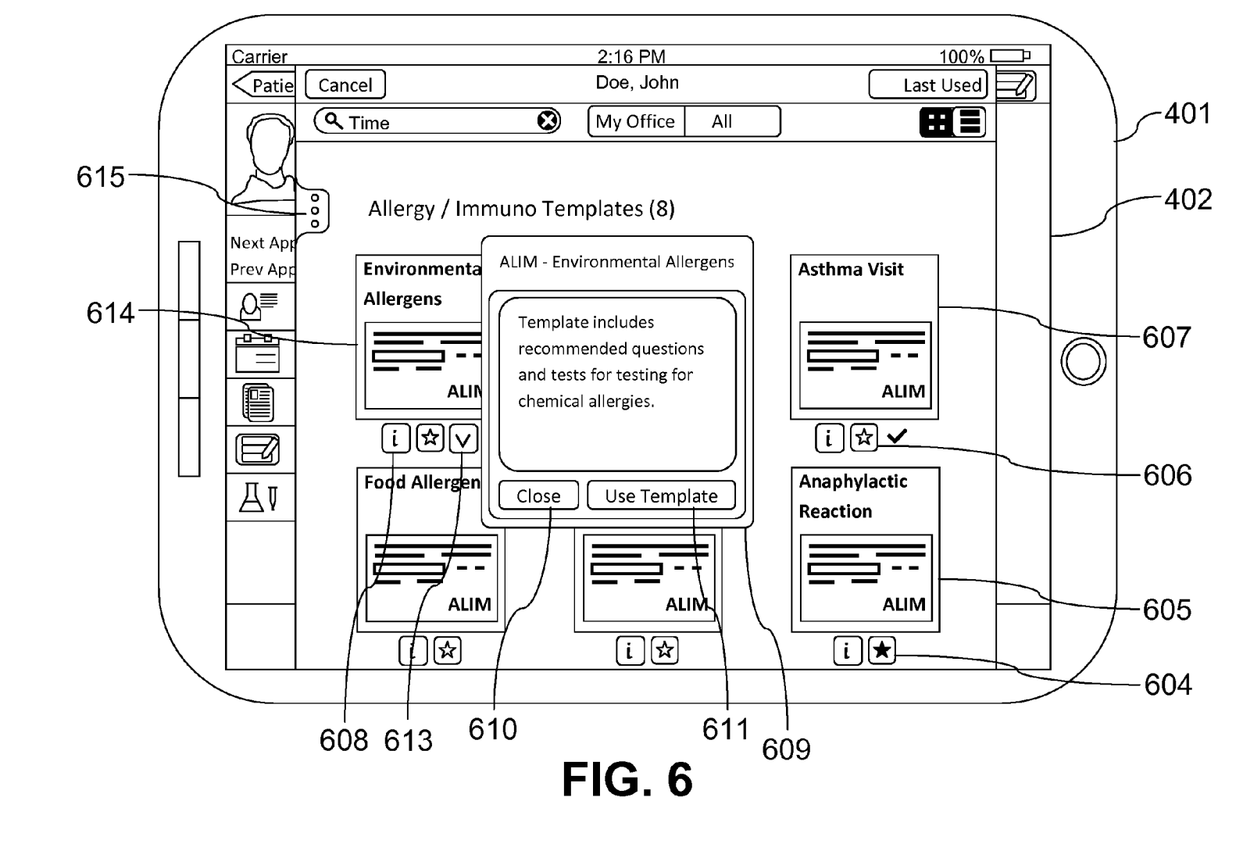
FIG. 6 is an illustration of an embodiment in which a user pop-up window with information about a template is presented.

FIG. 6 is an illustration of an embodiment in which additional functionality of the template selection screen is demonstrated. First favorites list icon 604 is associated with a first particular template icon 605. Second favorite list icon 606 is associated with second particular template icon 614. Favorites list icon 604 has a certain appearance because template icon 605 is on a template favorites list. Favorites list icon 606 has a different appearance because template icon 607 is not on the template favorites list. The user is able to quickly identify and manage favorite templates easily via favorite icons. Information icon 608 is associated with template icon 607. When information icon 608 is selected, template information pop-up window 609 is presented on display 402. Template information pop-up window 609 provides information about the clinic note template with which template icon 614 is associated. By selecting use template button 611, the user is presented with a clinic note formatted according to the selected clinic note template. If the user decides the clinic note template is not the one desired, close button 610 allows the user to dismiss template information pop-up window 609. Download icon 613 indicates that the clinic note template represented by associated template icon 614 has been downloaded to a digital storage segment on user device 401 but not yet used. Expandable sidebar tab 615 is shown.

Figure 7:
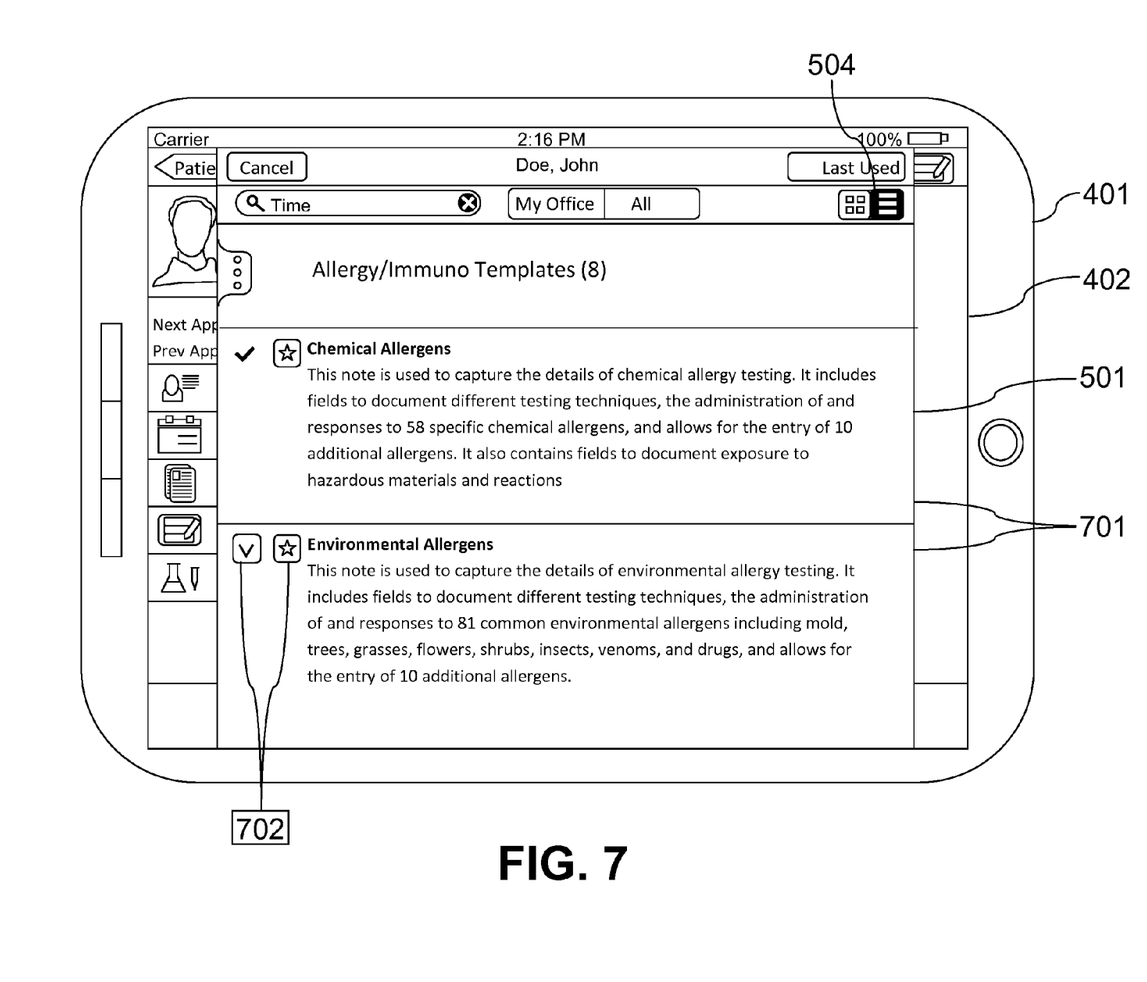
FIG. 7 is an illustration of an embodiment in which a user device presents a list view of template representations.

FIG. 7 is illustration of an embodiment in which template selection screen 501 in a list view. List elements 701 describe the clinic note templates. Each list element has plurality of secondary icons 702 associated with it. In list view, view selector icon 504 indicates that the view is in list form.

Figure 8:
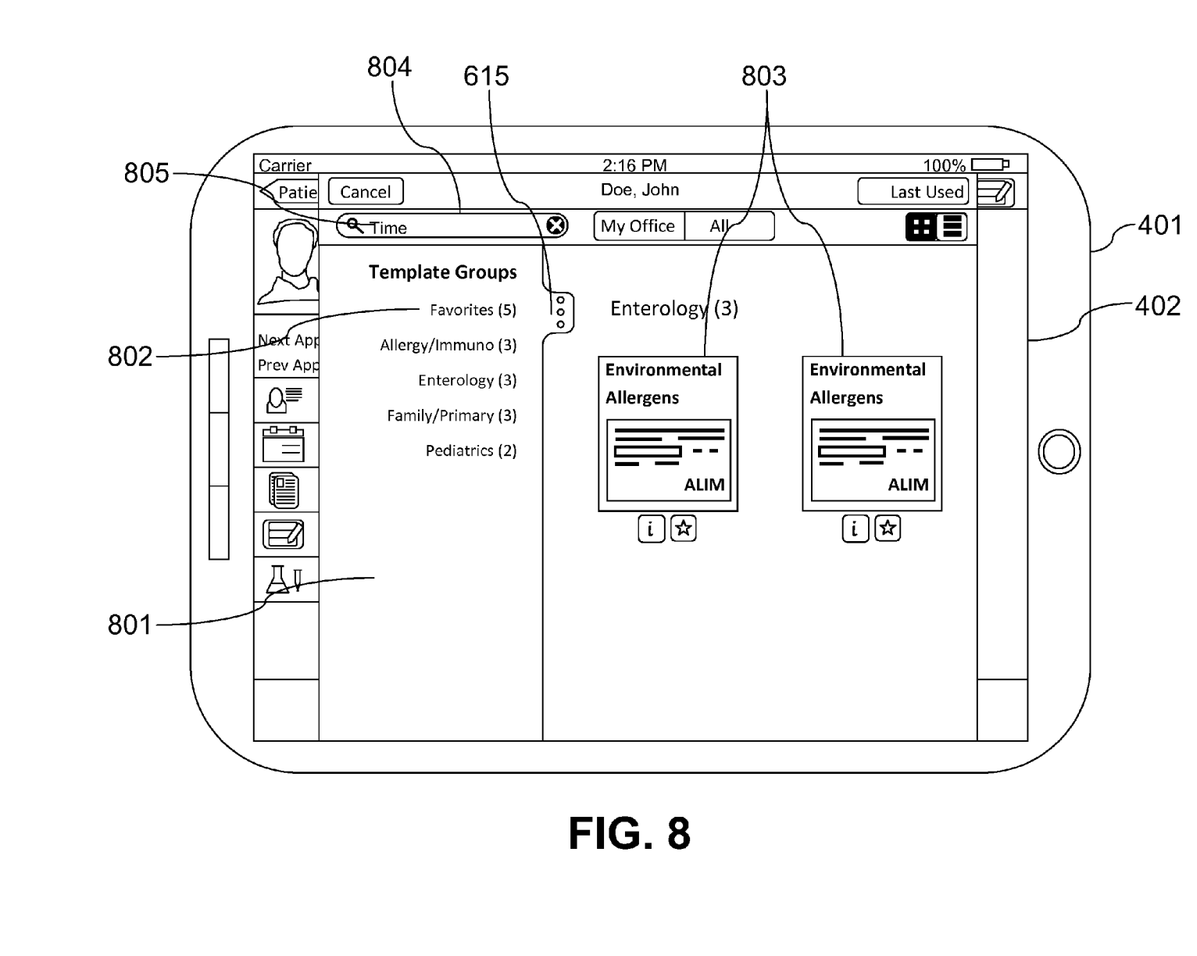
FIG. 8 is an illustration of an embodiment in which a sidebar containing categories of templates is presented.

FIG. 8 is an illustration of an embodiment in which sidebar 801 is expanded. Sidebar 801 can be expanded or contract through the use of expandable sidebar tab 615. Sidebar 801 contains a categorical listing. Each particular category in the categorical listing is associated with a plurality of clinical note templates. In the embodiment, the favorites category is associated with the templates favorites list and selecting it will display representations of the clinic note templates that are on the templates favorite list. The number of clinic note templates associated with each category is displayed in parentheses next to the category. When particular category 802 is selected, representations 803 of the clinic note templates associated with the particular category are presented in the graphical user interface. Search box 804 allows a user to search the clinic note templates for a particular template by entering a search term 805 in search box 804.

Figure 9:
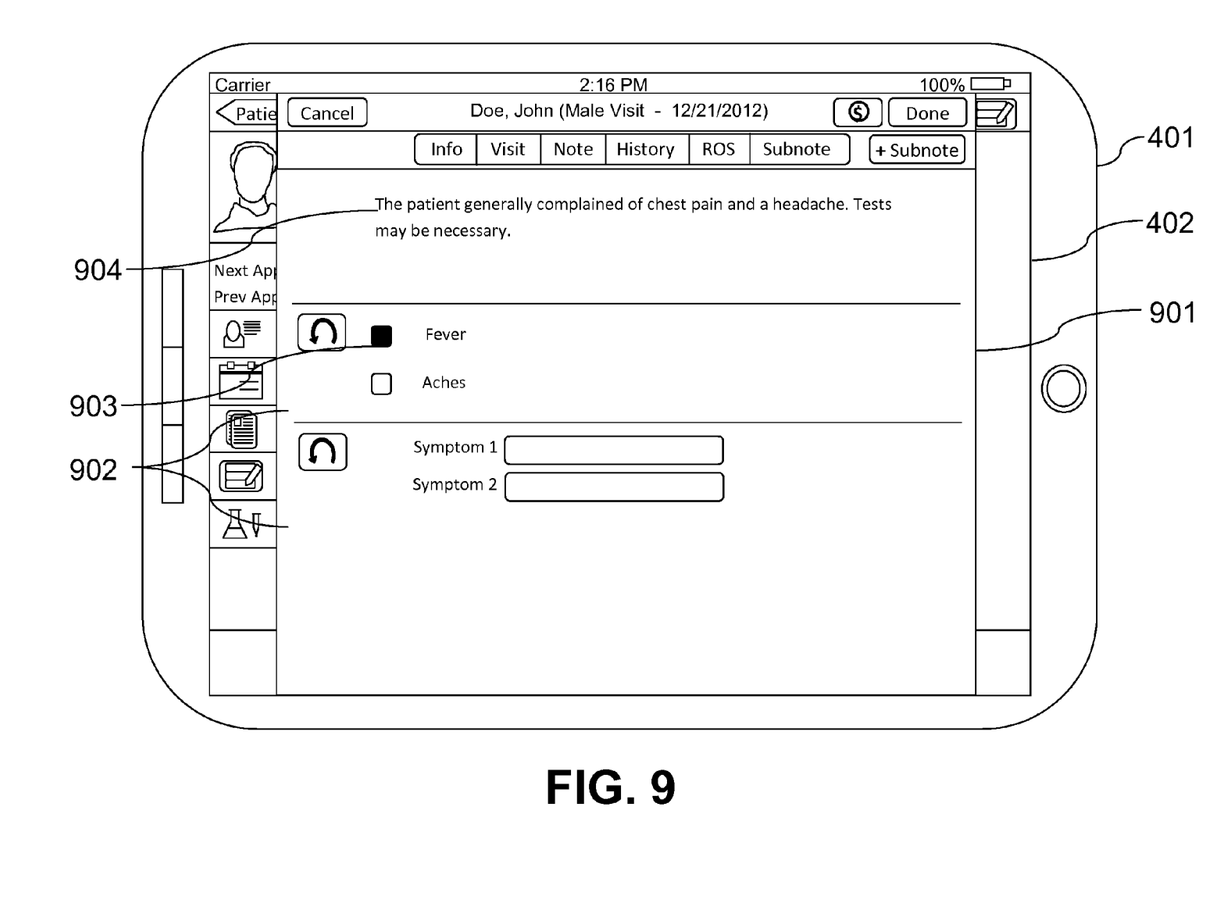
FIG. 9 is an illustration of an embodiment in which a clinic note is presented as formatted according to a clinic note template.

FIG. 9 is an illustration of an embodiment in which clinic note 901 is presented on display 402. Clinic note 901 is formatted according to a particular clinic note template selected by the user. Clinic note 901 has fields 902. Device 401 manipulates fields 902 according to received user input.

Figure 10:
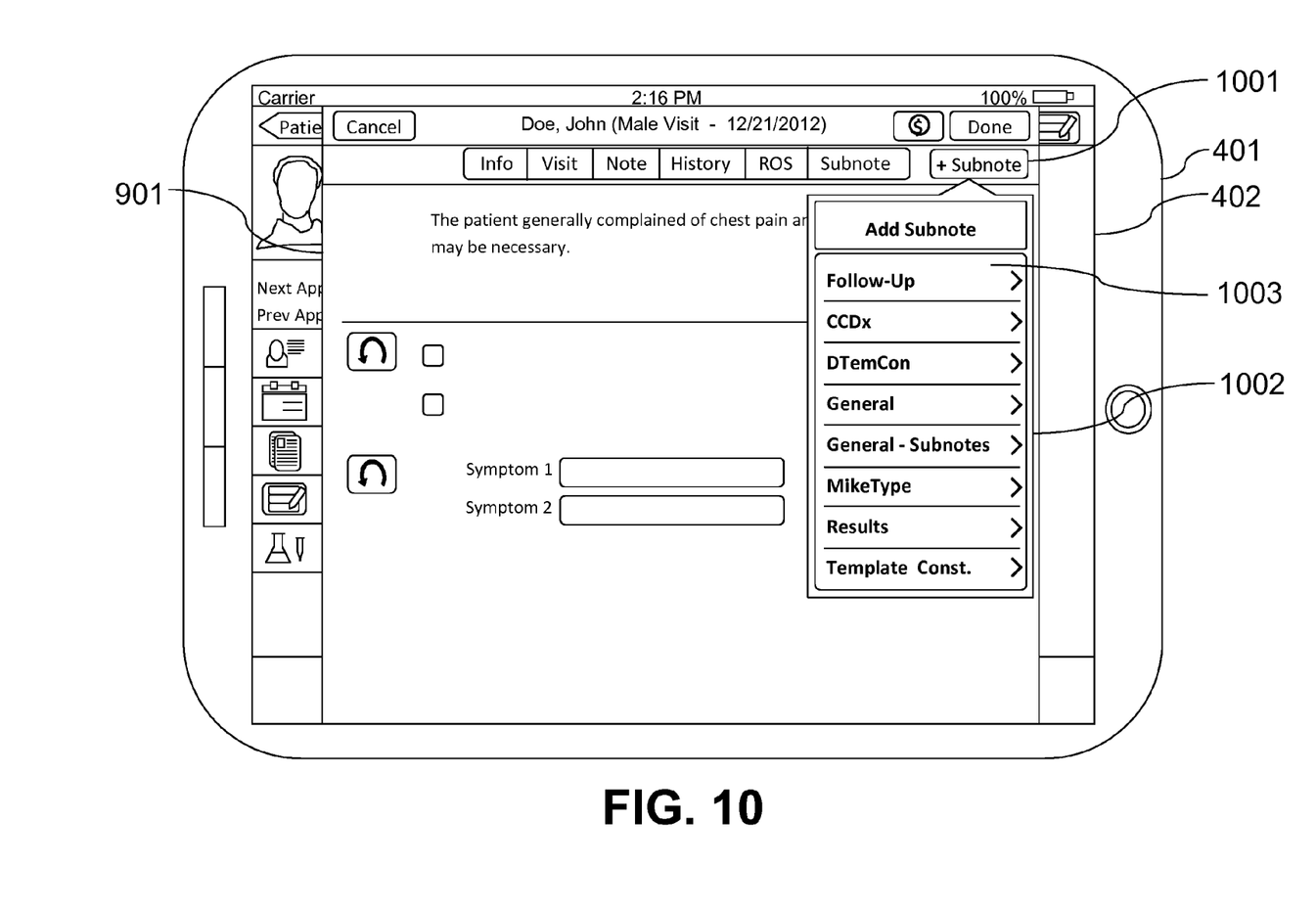
FIG. 10 is an illustration of an embodiment in which a subnote drop-down menu is presented.
Figure 11:
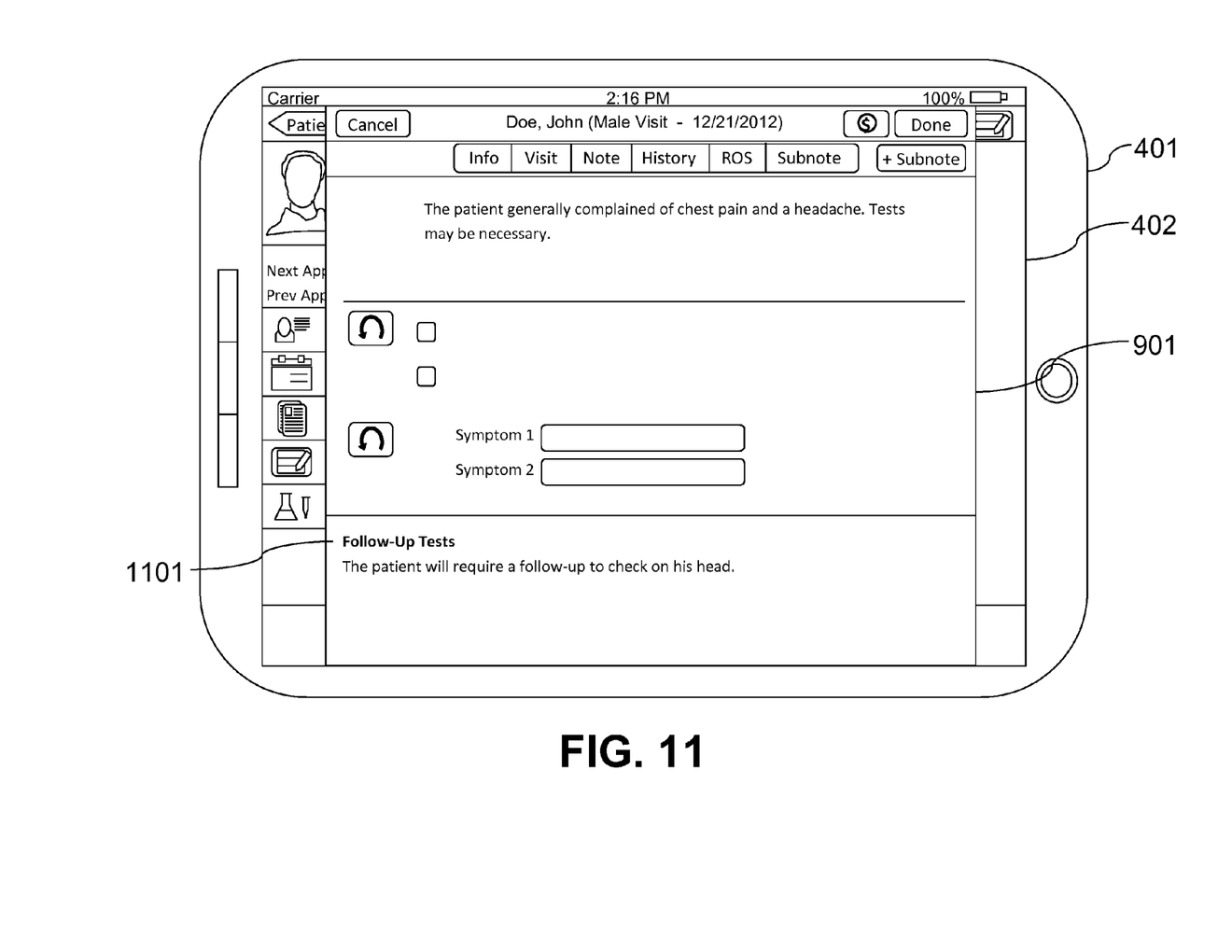
FIG. 11 is an illustration of an embodiment in which a subnote is pinned to a clinic note.

FIGS. 10 and 11 are illustrations of an embodiment and the functionality of subnotes. Subnote button 1001, when selected, causes subnote drop down window 1002 to be presented on display 402. When the user selects particular subnote 1003 to be added to the clinic note, a subnote is "pinned" or affixed to the bottom of clinic note 901. FIG. 11 illustrates clinic note 901 with subnote 1101. The user can add subnote 1101 to a clinic note even after the clinic note has been finalized, so that additional information or needed further action can be collected. Subnote 1101 is saved and encoded onto a digital storage segment such that it remains associated with clinic note 901.

Figure 12:
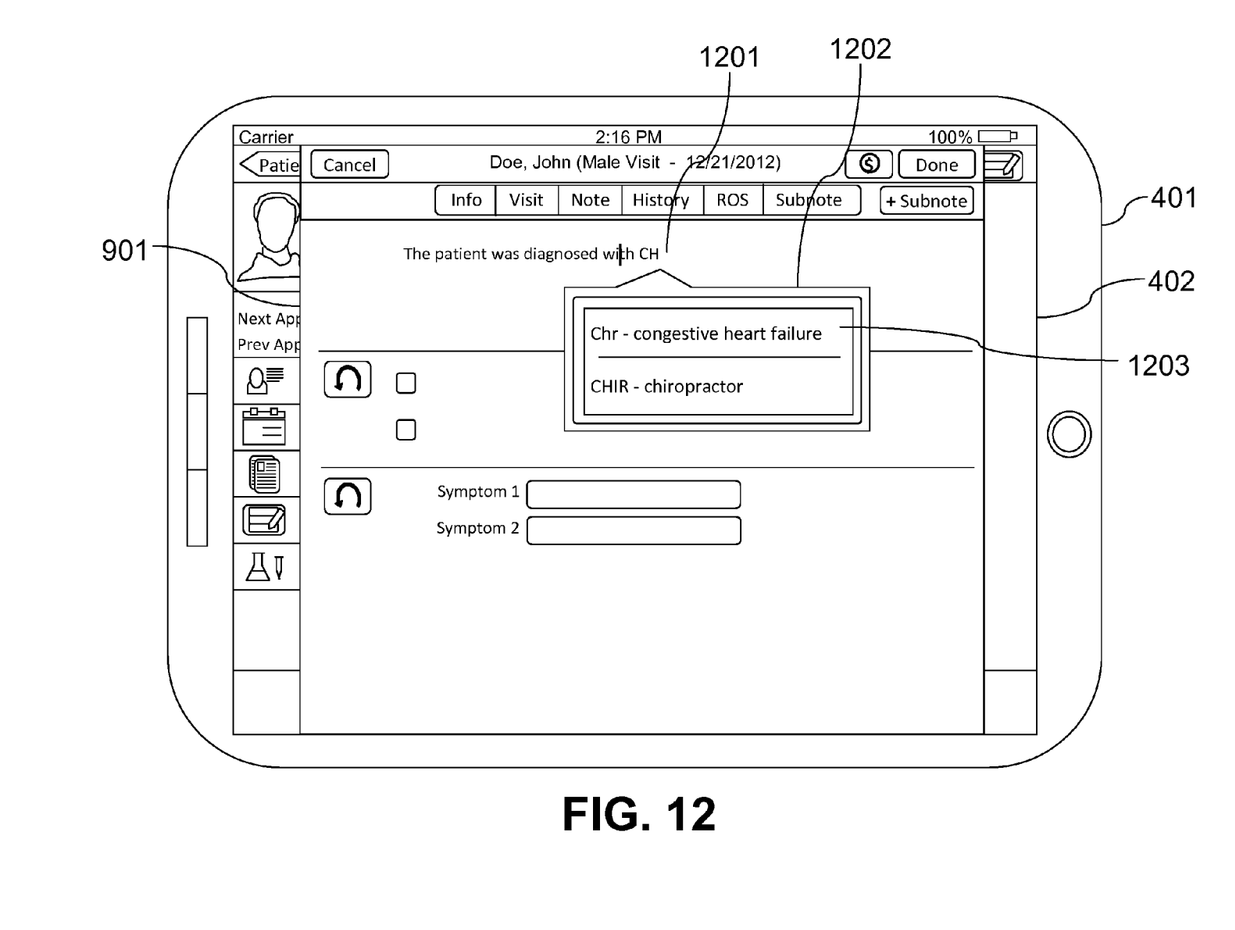
FIG. 12 is an illustration of an embodiment in which an acronym expansion pop-up window is presented.

FIG. 12 is an illustration of an embodiment demonstrating the functionality of automatic acronym extension. When a user inputs portion of a string of textual input 1201 that is a portion of an acronym the processor of user device 401 is effective to discern that such a portion of an acronym has been entered. The processor of user device 401 is effective to present on display 402 pop-up window 1202 containing acronyms which could correspond to the portion of a string of textual input. When the user selects particular expanded acronym 1203, particular expanded acronym 1203 is inserted into clinic note 901.

Figure 13:
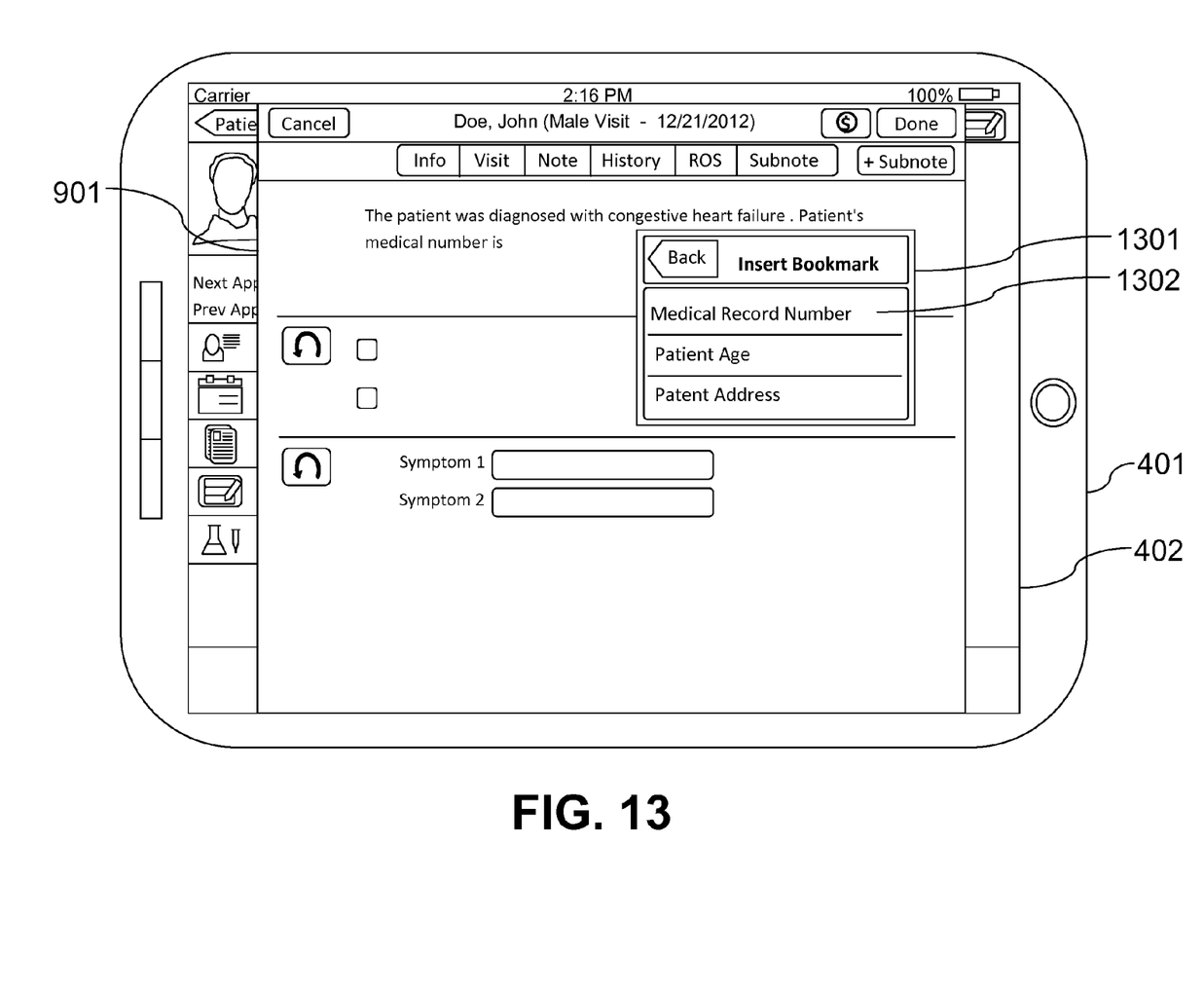
FIG. 13 is an illustration of an embodiment in which a pop-up window containing information bookmarks is presented.
Figure 14:
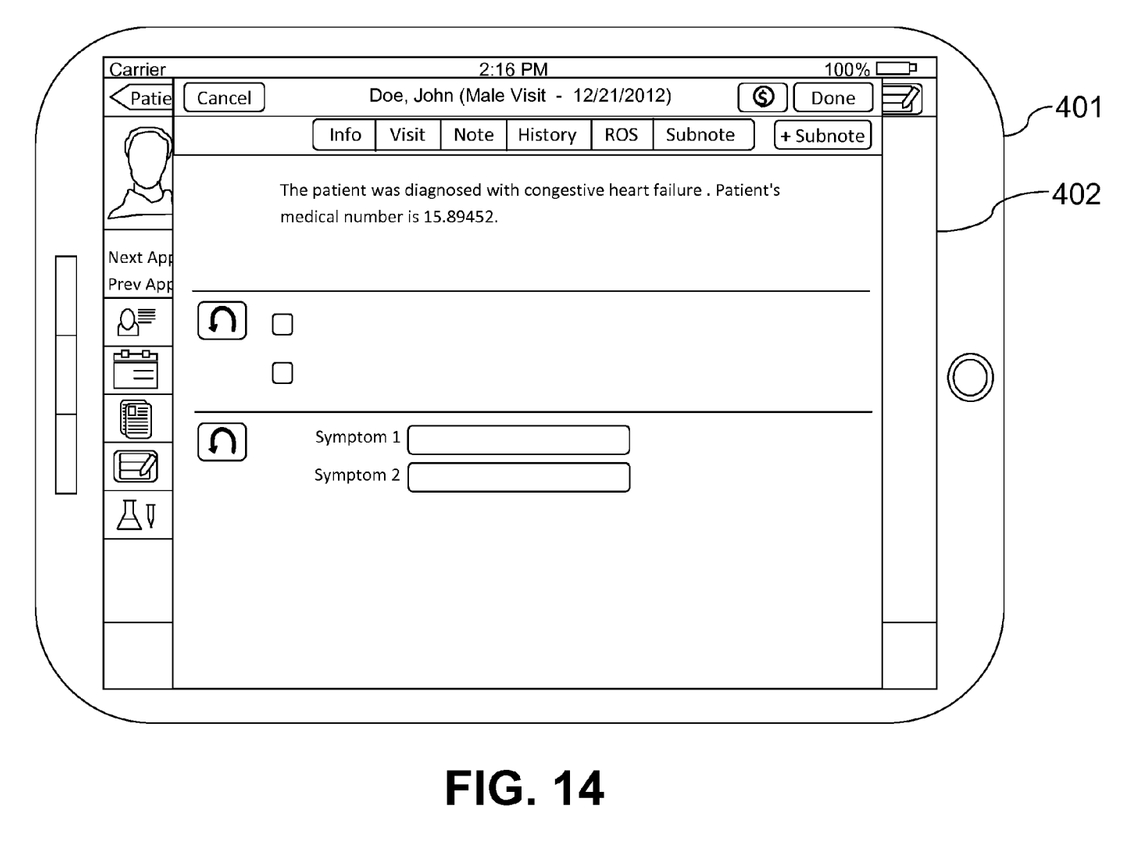
FIG. 14 is an illustration of an embodiment in which bookmarked information from a patient's electronic health record is inserted into a clinic note.

FIGS. 13-14 together illustrate an embodiment and demonstrate the functionality of the insertion of bookmarked information about a patient. When user input is received by user device 401 that a bookmarked piece of information is desired, bookmark window 1301 is presented. Certain information about a patient, such as age, sex, or patient number, can be automatically bookmarked by the system. When the user selects particular book mark 1302, the processor of user device 401 pulls the desired health information from the patient's EHR and inserts the desired information into the clinic note. This prevents the user from needing to navigate multiple screens to collect standard information. It also helps ensure accurate data entry. FIG. 14 illustrates the entered bookmarked information.

The foregoing description of preferred and other embodiments is not intended to limit or restrict the scope or applicability of the inventive concepts conceived of by the Applicants. In exchange for disclosing the inventive concepts contained herein, the Applicants desire all patent rights afforded by the appended claims. Therefore, it is intended that the appended claims include all modifications and alterations to the full extent that they come within the scope of the following claims or equivalents thereof.

What is claimed is:

1. An electronic health record system, comprising:
   an electronic device having a display and being capable of receiving user input;
   a first digital storage segment;
   a plurality of clinic note templates encoded on the first digital storage segment;
   a second digital storage segment;
   a plurality of electronic health records encoded on the second digital storage segment, each record associated with a particular patient;
   said electronic device effective to access the clinic note templates on the first storage segment and present on the display a template selection screen;
   said template selection screen containing a plurality of representations of at least a portion of the clinic note templates,
   wherein said electronic device is effective to present on the display a clinic note formatted according to a particular clinic note template and containing a plurality of fields when the user device receives user input that a user representation of a particular clinic note template is selected;
   said electronic device effective to receive a user input that a particular field should be manipulated; and
   said electronic device further effective to present on the display a manipulated field according to the particular user input, wherein:
   said user input is a portion of a string of textual input;
   said processor of the user device effective to discern that said portion of a string of textual input is a portion of an acronym;
   said device effective to present on the display a pop-up window containing a plurality of optional expanded acronyms and receive a second user input that one of said plurality of optional expanded acronyms has been selected; and
   said device effective to present on the display a completed string of textual input.

2. The system of claim 1, further comprising:
   said template selection screen containing a sidebar including a categorical listing; and
   said electronic device effective to present on the display a set of clinic note template representations associated with a particular category included in the categorical listing when the user device receives a user input that the particular category is selected.

3. The system of claim 2 wherein said sidebar can be collapsed on the display.

4. The system of claim 1 wherein:
   said representations are template icons of the same size; and
   each template icon having a plurality of associated and proximate secondary icons presented on the display.

5. The system of claim 4 wherein:
   one said plurality of secondary icons is a favorites list icon; and
   said favorites list icon having a first appearance if the clinic note template with which the favorite list icon is associated is on a template favorites list and a second appearance if the clinic note template with which the favorite list icon is associated is not on the template favorites list.

6. The system of claim 5 wherein the electronic device is effective to add the clinic note template associated with a favorites list icon to the template favorites list when the electronic device receives user input that the favorites list icon has been selected.

7. The system of claim 4 wherein one of the plurality of secondary icons is an information icon;
   said electronic device effective to present on the display an information popup window when said electronic device receives user input that said information icon has been selected.

8. The system of claim 1 wherein:
   said representations are textual list elements; and
   each said textual list element having a plurality of secondary icons associated with it.

9. The system of claim 1 wherein said plurality of clinic note templates can be searched for a particular clinic note template.

10. The system of claim 1 wherein said first and second digital storage segments are portions of a single digital storage medium.

11. The system of claim 1, further comprising:
    said electronic device is effective to receive a user input that a subnote should be pinned to the bottom of said clinic note; and
    said electronic device further effective to present on the display a subnote that is pinned to the bottom of said clinic note.

12. The system of claim 1 wherein:
    said user input is an instruction that a bookmarked information window should be presented on the display;
    said user device effective to present on the display the bookmarked information window containing a plurality of bookmarks, each bookmark associated with a piece of information from the electronic health record of a particular patient;
    said user device effective to receive a second user input that a particular bookmark is selected and present on the display a manipulated field containing the piece of information associated with the particular bookmark.

13. A method of managing electronic health records and creating electronic clinic notes, comprising:

providing an electronic device having a display and being capable of receiving user input;
providing a first digital storage segment;
providing a second digital storage segment;
encoding on said first digital storage segment a plurality of clinic note templates;
encoding on said second digital storage segment a plurality of electronic health records, each record associated with a particular patient;
accessing said clinic note templates on said electronic device;
presenting on said display a template selection screen containing a plurality of representations of at least a portion of the clinic note templates,
wherein said electronic device is effective to present on the display a clinic note formatted according to a particular clinic note template and containing a plurality of fields when the user device receives user input that a user representation of a particular clinic note template is selected;
said electronic device effective to receive a user input that a particular field should be manipulated; and
said electronic device further effective to present on the display a manipulated field according to the particular user input, wherein:
said user input is a portion of a string of textual input;
said processor of the user device effective to discern that said portion of a string of textual input is a portion of an acronym;
said device effective to present on the display a pop-up window containing a plurality of optional expanded acronyms and receive a second user input that one of said plurality of optional expanded acronyms has been selected; and
said device effective to present on the display a completed string of textual input.

14. The method of claim 13 wherein said representations are template icons of the same size, each template icon having a plurality of associated and proximate secondary icons presented on the display.

15. The method of claim 13 wherein said representations are textual list elements, each said textual list element having a plurality of secondary icons associated with it.

16. The method of claim 13 wherein said electronic device is effective to present on the display a clinic note formatted according to a particular clinic note template and containing a plurality of fields when the user device receives user input that a user representation of a particular clinic note template is selected.

17. The method of claim 16 further comprising:
receiving user input on said electronic device that a particular field should be manipulated; and
presenting on said display a manipulated field according to the user input.

* * * * *